United States Patent [19]

Køhnke

[11] 4,029,093
[45] June 14, 1977

[54] GAS SUPPLY DEVICE

[75] Inventor: Øle Bjørn Køhnke, Kgs. Lyngby, Denmark

[73] Assignee: Ruth Lea Hesse, Rungstead Kyst, Denmark

[22] Filed: Sept. 19, 1975

[21] Appl. No.: 614,954

[30] Foreign Application Priority Data

Sept. 20, 1974 Sweden .............................. 7411882

[52] U.S. Cl. ........................... 128/145.7; 128/145.8
[51] Int. Cl.² ........................................ A61M 16/00
[58] Field of Search ......... 128/145.7, 145.5, 145.6, 128/145.8, 142, 203, 188, 196, 197, 209, 210, 266, 277; 137/604; 431/173; 239/403

[56] References Cited
UNITED STATES PATENTS

| 1,312,117 | 8/1919 | Hinkle ................................. 128/196 |
| 1,517,598 | 12/1924 | Stevenson ........................... 137/604 |
| 3,262,446 | 7/1966 | Stoner ............................... 128/145.8 |

Primary Examiner—Robert W. Michell
Assistant Examiner—Henry J. Recla
Attorney, Agent, or Firm—Spencer & Kaye

[57] ABSTRACT

A device for administering to a patient a mixture of a first gas and at least one second gas in a desired, predetermined ratio between 0 and 100%, includes a self-expanding, lung-venting bladder having an inlet through which the gases are introduced into the bladder and an outlet through which the gases are administered to a patient, and a check valve controlling the bladder inlet for preventing the gases from escaping from the bladder through the bladder inlet. The first gas is supplied to the device by a non-pressurized system, while the second gas is supplied under pressure. The bladder is adapted to expand for drawing the gases thereinto through the bladder inlet and to be compressed for discharging the gases therefrom through the bladder outlet. The device further includes a suction valve which has a housing defining a chamber; a valve outlet disposed centrally with respect to the chamber and connected to the bladder inlet for maintaining communication between the chamber and the bladder inlet. The suction valve also has a suctional intake opening positioned radially outwardly of the valve outlet and continuously communicating with the non-pressurized system; and at least one inlet nozzle supported adjacent the suctional intake opening and oriented tangentially with respect to the chamber for injecting the second gas tangentially into the chamber. The inlet nozzle is arranged for controlling, by means of the second gas, the intake of the first gas by changing the pressure drop between the suctional intake opening and the valve outlet.

9 Claims, 15 Drawing Figures

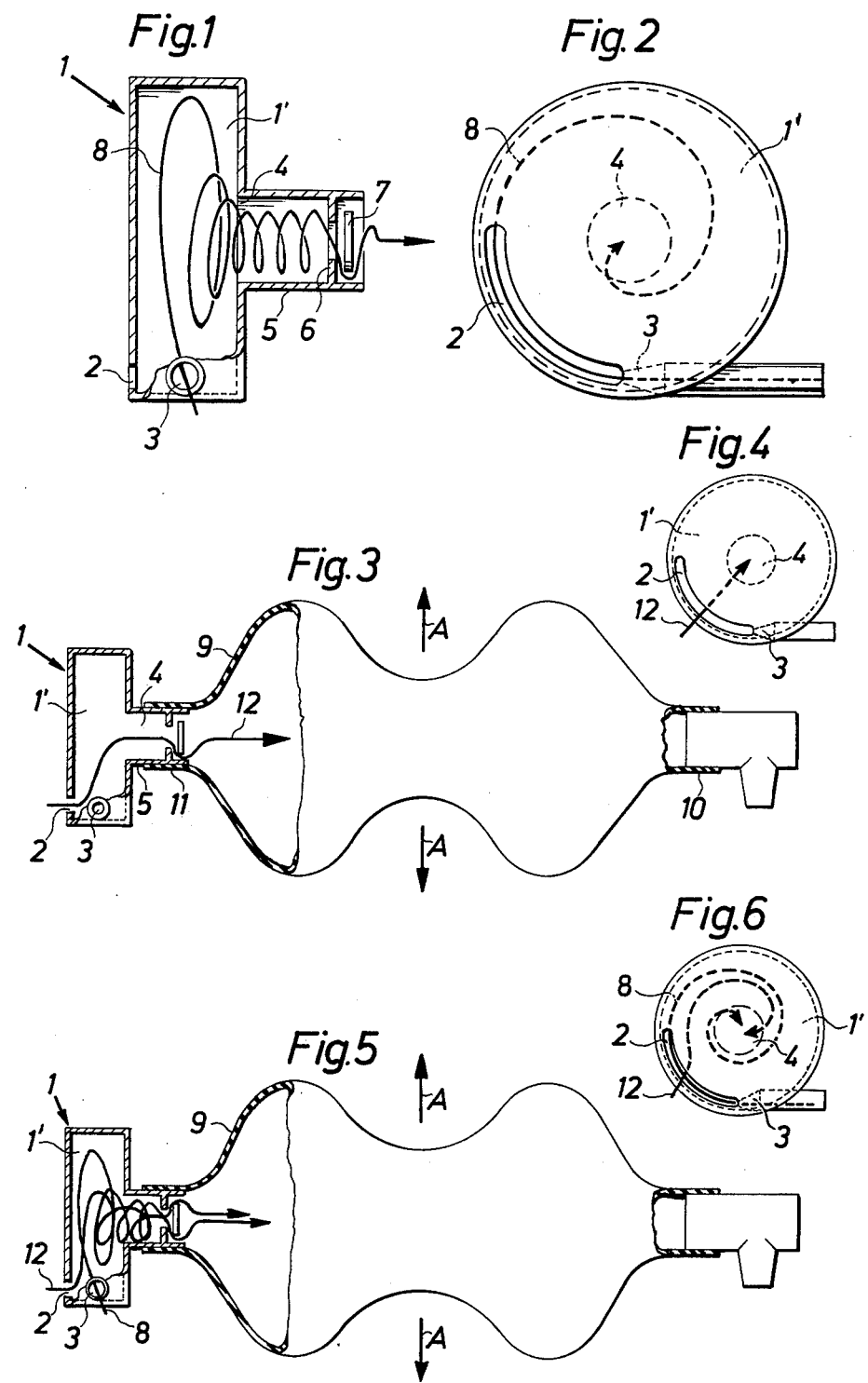

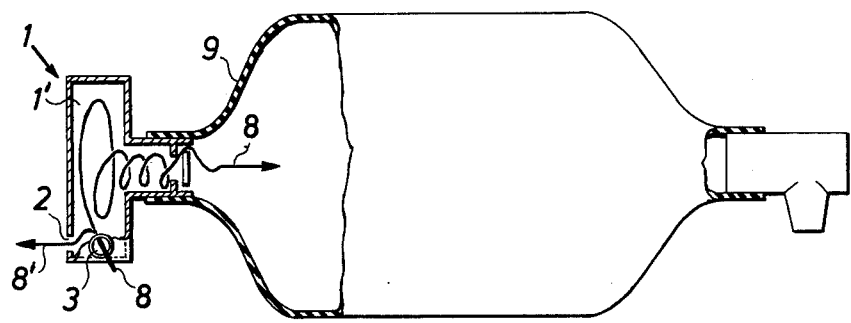
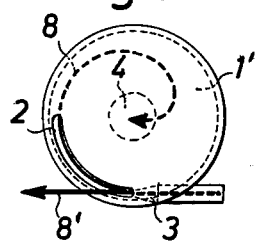 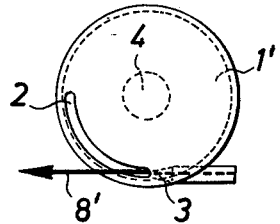
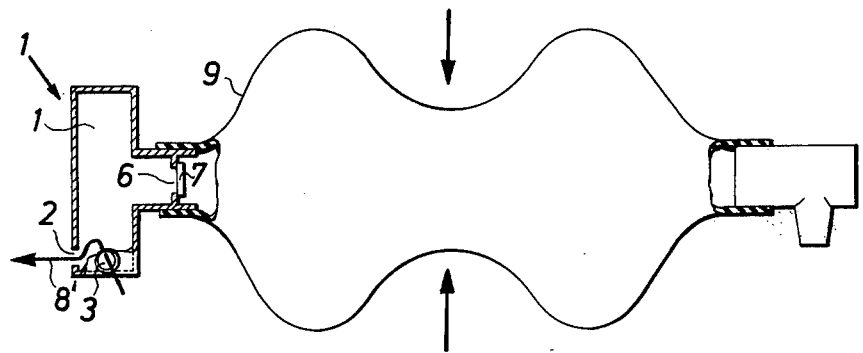

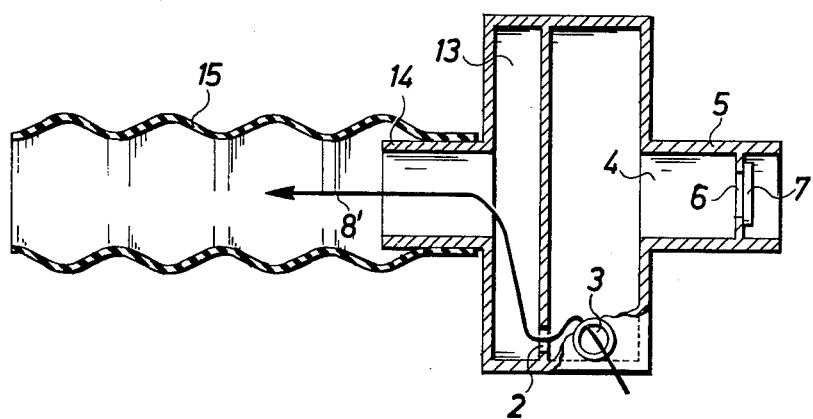
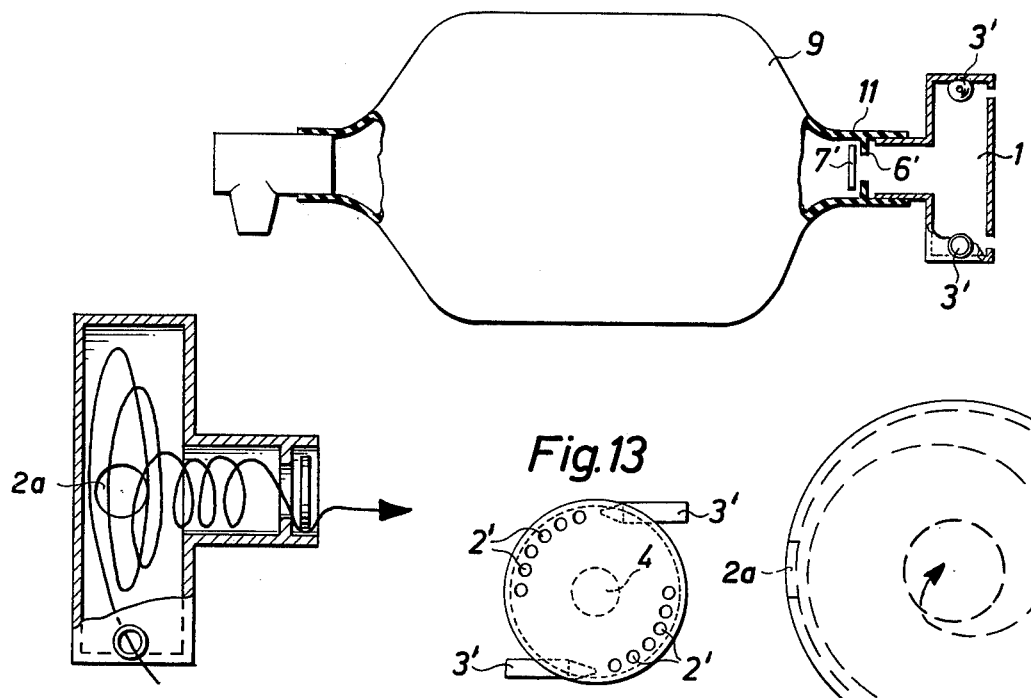

GAS SUPPLY DEVICE

BACKGROUND OF THE INVENTION

The invention relates to a device for suctional intake and forced discharge to a patient of one or several treating gases, or a mixture thereof. One of the gases is taken from a non-pressurized system. The device comprises a self-expanding lung-venting bladder, i.e. a bladder which automatically resumes its original shape after a compression. The bladder has an inlet provided with a check valve enabling treating gas such as atmospheric air and/or another gas to be sucked into the bladder, and an outlet leading to the patient, for example via a three-way breathing valve connected to a breathing mask or similar device either directly or via a connecting conduit. Such a self-expanding bladder fundamentally operates as follows:

When the bladder is compressed, the gas contained therein is expelled through the outlet valve and further to the respiratory ducts of the patient via the breathing mask. Thereafter the bladder is released and regains its original shape by virtue of its self-expanding property thereby causing a subatmospheric pressure to be formed within the bladder. Due to this subatmospheric pressure the bladder will again be filled with gas through the inlet valve whereafter a new insufflation may be performed.

In venting systems of this type it is often desirable to supply, in addition to the main gas fed through the suction valve, a treating gas, such as oxygen or narcosis gas. It is also desirable that the main gas and the additional gas be mixable in arbitrary proportions. In known systems such a gas is added via a separate valve opening into the bladder. As such additional gases are supplied under relatively high pressure (1 – 3 atmospheres) particular safety measures must be taken to prevent the patient from being exposed to harmful excess pressures due to the supply of the additional gas. This problem has, so far, not been solved in a satisfactory way.

SUMMARY OF THE INVENTION

It is an affect of the present invention to provide a device for suctional intake and forced discharge of gas wherein a main gas stream is to be mixed with at least one additional gas stream in arbitrary proportions, i.e. in continuous variation from 100% main gas to 100% additional gas, without any risk of impermissible excess pressures in the system due to the supply pressure of the additional gas.

This object and others to become apparent as the specification progresses, are accomplished by the invention, according to which, briefly stated, a device for administering to a patient a mixture of a first gas and at least one second gas in a desired, predetermined ratio between 0 and 100%, includes a self-expanding, lung-venting bladder having an inlet through which the gases are introduced into the bladder and an outlet through which the gases are administered to a patient, and a check valve controlling the bladder inlet for preventing the gases from escaping from the bladder through the bladder inlet. The first gas is supplied to the device by a non-pressurized system, while the second gas is supplied under pressure. The bladder is adapted to expand for drawing the gases thereinto through the bladder inlet and to be compressed for discharging the gases therefrom through the bladder outlet. The device further includes a suction valve which has a housing defining a chamber; a valve outlet disposed centrally with respect to the chamber and connected to the bladder inlet for maintaining communication between the chamber and the bladder inlet. The suction valve also has a suctional intake opening positioned radially outwardly of the valve outlet and continuously communicating with the non-pressurized system; and at least one inlet nozzle supported adjacent the suctional intake opening and oriented tangentially with respect to the chamber for injecting the second gas tangentially into the chamber. The inlet nozzle is arranged for controlling, by means of the second gas, the intake of the first gas by changing the pressure drop between the suctional intake opening and the valve outlet.

In the valve construction according to the invention there is formed upon supply of additional gas under pressure, a vortex flow between the tangentially disposed inlet nozzle or inlet nozzles and the central outlet opening. Since the pressure drop caused by this vortex flow becomes effective substantially only in the range between the outlet opening and the suctional intake opening or part of such an intake opening which radially is closest to the outlet opening, the suctional intake opening or openings are preferably provided along an arc of a circle having the same center as the outlet opening. In this connection it is particularly suitable to dispose the suctional intake opening or openings, which preferably are in the form of a slot, along the periphery of the eddy chamber.

The suction valve forming a part of the device according to the invention operates in the following way:

The outlet opening is connected to the inlet of the self-expanding venting bladder and the inlet nozzle or nozzles are connected to a source of a suitable additional gas, such as a pressure container for $O_2$. The supply of additional gas is controlled in a way known in itself by means of a suitable valve such as a conventional throttle valve.

When the venting bladder during its phase of expansion sucks in main gas such as atmospheric air through the suctional intake opening or openings, the sucked-in main gas normally — i.e. when no additional gas is supplied — will flow radially through the vortex chamber through the central outlet opening and into the venting bladder via the check valve without any appreciable pressure drop in the vortex chamber. The self-expanding venting bladder will under these conditions draw exclusively main gas at a rate determined by the resilient properties of the self-expanding bladder and the pressure drop through the complete inlet valve under conditions of unhampered flow.

However, if an additional gas such as $O_2$ is supplied from a pressure source through the tangentially disposed nozzle or nozzles, the additional gas will form a vortex flow propagating helically from the nozzle or nozzles towards the center. As known for vortex currents, a pressure differential is thereby produced between the nozzle or nozzles and the center where the outlet opening is provided so that the pressure in the center is lower than the pressure along the periphery where the nozzle or nozzles and the suctional intake openings are provided. When the dimensions of the vortex chamber and the inlet nozzles as well as the size of the suctional intake openings and the central outlet opening are given, the magnitude of this pressure differential is exclusively dependent on the amount of additional gas supplied through the tangential inlet nozzle or nozzles.

When such an additional gas is supplied from a pressure source through the tangential inlet nozzles during the suction phase of the venting bladder, an equilibrium is formed between the amount of main gas and the amount of additional gas draw in the bladder because the resiliency of the bladder generates a characteristic underpressure at the central outlet opening of the vortex chamber. At the suctional intake openings which are positioned farther outwardly in relation to the outlet opening, preferably at the periphery of the vortex chamber, this underpressure, however, will be reduced due to the pressure distribution in the vortex. In this way the rate at which the main gas is sucked into the vortex chamber through the suctional intake openings and which is determined by the magnitude of the underpressure prevailing at the suctional intake openings, will depend on the amount of this additional gas supplied to the vortex chamber through the tangential inlet nozzles. To the same extent as the amount of the supplied additional gas gas supplied increases, the amount of the drawn-in main gas will decrease and the proportion of the additional gas received by the bladder will increase.

When the amount of the additional gas has been increased to a certain value, the pressure differential between the suctional intake openings and the outlet opening will be equal to the underpressure formed at the central outlet opening due to the resiliency of the bladder. The underpressure at the suctional intake opening then becomes O. The vortex formed by the additional gas will then prevent main gas to be sucked into the bladder at all which in this case will be filled exclusively with additional gas. The filling time for the self-expanding venting bladder will in this case be equal to the time required to supply the amount of additional gas necessary to completely fill the venting bladder in its fully expanded state.

By varying the amount of the additional gas supply it is thus possible to continuously vary its proportion between 0% and 100%, the expansion time of the venting bladder being shortest at 0% and longest at 100% of additional gas.

When the expansion of the self-expanding venting bladder has come to an end there will be a flow division of the additional gas in such a way that part thereof flows through the central outlet opening and into the venting bladder whereas the rest flows out from the vortex chamber through the suctional intake openings.

During the compression phase of the venting bladder the excess pressure in the bladder will close the check valve positioned between the central outlet opening of the vortex chamber and the venting bladder. Thereby the vortex formed by the additional gas will be destroyed, and all of the additional gas is forced to flow out through the suctional intake openings without appreciable pressure drop.

In the valve construction according to the invention the lungs of the patient thus can never be exposed to the dangerously high supply pressure of the additional gas. As it is desirable to use also the part of the additional gas flowing out backwardly through the suctional intake openings during the rest and compression phases of the bladder, the intake valve may be provided with a relatively small gas collecting container in which the additional gas is collected during the rest and compression phases to be suction in later in place of or together with the main gas.

The bladder-and-valve unit structured according to the invention operates in a particularly reliable manner due to the lack of moving parts, and further, its cleaning may be effected with ease.

BRIEF DESCRIPTION OF THE DRAWINGS

FIG. 1 is a schematic sectional side elevational view of a preferred embodiment of a suction valve structured according to the invention;

FIG. 2 is a schematic front elevational view of the structure illustrated in FIG. 1;

FIG. 3 is a schematic sectional side elevational view of the suction valve according to FIGS. 1 and 2 in combination with a self-expanding venting bladder and with the direction of flow indicated during the expansion phase of the bladder when no addition gas is supplied;

FIG. 4 is a schematic front elevational view of the suction valve shown in FIG. 3 with an indication of the flow path;

FIGS. 5 and 6 correspond to FIGS. 3 and 4 respectively but show the flow direction during the expansion phase of the bladder when additional gas is supplied;

FIGS. 7 and 8 correspond to FIGS. 3 and 4, respectively showing the flow distribution of the additional gas during the rest phase of the bladder;

FIGS. 9 and 10 correspond to FIGS. 3 and 4, respectively but show the flow direction of the additional gas during the compression phase of the bladder;

FIG. 11 is a schematic sectional side elevational view of another preferred embodiment of the suction valve supplied with a gas-collecting container;

FIG. 12 is a schematic sectional side elevational view of a further preferred embodiment in which a check valve element is disposed on the venting bladder rather than on the suction valve itself; and FIG. 13 is a schematic end front elevational view of the suction valve shown in FIG. 12;

FIG. 14 is a schematic sectional side elevational view of a further preferred embodiment of a suction valve according to the invention; and FIG. 15 is a schematic front elevational view of the structure illustrated in FIG. 14.

DESCRIPTION OF THE PREFERRED EMBODIMENTS

The suction valve illustrated in FIGS. 1 and 2 comprises a housing 1 enclosing a cylindrical vortex chamber 1' having a peripheral suctional intake opening 2 shaped as a slot extending along an arc of a circle and a central outlet opening 4. An inlet nozzle 3 discharges tangentially into the vortex chamber 1' and is adapted to be connected to a pressure source (not shown) for an additional gas. The central outlet opening 4 in this embodiment is extended by a tubular connecting stud 5 containing a check valve composed of a valve seat 6 and a movable valve element 7. This check valve which permits flow only in the direction from the vortex chamber 1' may be of conventional structure. In FIGS. 1 and 2 arrow 8 indicates schematically the flow path of the additional gas from nozzle 3 when check valve 6, 7 is open during the expansion phase of the venting bladder. In FIG. 3 the suctional intake valve according to the invention is shown combined with a conventional, self-expanding venting bladder 9, the outlet end 10 of which can be conventionally connected to the respiratory duct of a patient, for example via a schematically shown three-way breathing valve of a well-known type. The connecting stud 5 of the suction valve is sealingly inserted into an inlet opening 11 of the venting bladder 9. FIGS. 3 and 4 illustrate the expansion phase (as indicated by arrows A) of the venting bladder under conditions in which no additional gas is supplied through the inlet nozzle 3. During this phase of operation the check valve 6, 7 is open and the suctionally aspired main gas flows substantially radially through the vortex chamber 1' from the suctional intake opening 2 to the central outlet opening 4 without any appreciable pressure drop from the periphery to the center. Thereafter the main gas flows through the connecting stud 5 and the check valve 6, 7 into the bladder 9. The flow path of the main gas is indicated in the drawings by reference designation 12.

FIGS. 5 and 6 illustrate the expansion phase of the venting bladder 9 when additional gas is supplied through nozzle 3. As appears from these FIGS., the additional gas flows spirally from nozzle 3 to outlet opening 4. Due to the vortex flow 8 of the additional gas, the main gas too will flow spirally from the suctional intake opening 2 to the central outlet opening 4. Due to the vortex flow in the vortex chamber 1' a pressure differential will appear between the suctional intake opening 2 and the central outlet opening 4. The greater the amount of additional gas supplied through nozzle 3, the greater the pressure differential will be between the suctional intake opening 2 and the outlet opening 4 and the lesser will be the driving underpressure at the suctional intake opening 2, causing a lesser proportion of main gas to be supplied to bladder 9. Simultaneously the time required to fill bladder 9 with a certain amount of gas will increase. When the amount of additional gas supplied is so large that the pressure differential in the vortex between the suctional intake opening 2 and the outlet opening 4 is equal to the underpressure generated at the central outlet opening 4 due to the expansion of bladder 9, the supply of main gas 12 to the bladder 9 will cease. This is so, because the driving pressure at the suctional intake opening 2 in this situation is O and the bladder will instead be filled exclusively with additional gas.

FIGS. 7 and 8 illustrate the flow conditions for the case when the bladder 9 is in its expanded condition of rest while additional gas is supplied from nozzle 3. In this case the additional gas is divided into two flow portions, the first of which — designated at 8 — flows through the central outlet opening 4 into the bladder 9 whereas the second flow portion-designated at 8' out "rearwardly" through the suctional intake opening 2.

FIGS. 9 and 10 illustrate the flow conditions of the additional gas during the compression phase of the bladder 9, i.e. while gas is injected into the patient. The overpressure in bladder 9 will cause the check valve 6, 7 to close, all the additional gas being forced to flow out rearwardly through the suctional intake opening 2 without appreciable pressure drop.

In FIG. 11 there is shown a suction valve according to the invention provided with a gas-collecting container 15 permitting recovery of additional gas which is discharged through suctional intake opening 2 during the rest and compression phases of the bladder. The suctional intake valve in this embodiment is provided with a pre-chamber 13 through which the main gas flows prior to passing during the suction phase through the suctional intake opening 2. The pre-chamber 13 is provided with a connecting stud 14 to which the gas-collecting container 15 is sealingly attached. The container 15 may, for example, conventionally be constructed as a hose which is open at the free end. When the additional gas 8' during the rest and compression phases of the bladder flows out through the suctional intake opening 2 it will be collected and accumulated in container 15 to be subsequently drawn in instead of or together with the main gas during the expansion phase of the bladder.

Obviously the invention is not restricted to the specific embodiments described above, but many variations and modifications are imaginable within the frame of the basic idea of the invention. For example, the way in which the valve is coupled to the venting bladder is not critical for the function of the valve. Thus, for example, it is not necessary that the check valve securing a flow only from the valve outlet into the bladder be provided on the valve element itself, this check valve may, instead be provided in the intake portion of the bladder itself. Such an alternative embodiment is shown in FIG. 12, in which the check valve elements 6' and 7' in the intake portion of bladder 9 perform the same function as valve element 6, 7 in the embodiments illustrated in FIGS. 1 to 11.

It is further not necessary to use a single suctional intake opening in the form of an arc of a circle. The same effect can be achieved by using two or several suctional intake openings disposed in a way different from the slot 2 shown in FIGS. 1 to 12 as easily understood by a person skilled in the field. The essential feature is that the suctional intake opening or openings are disposed radially outside the central outlet opening 4 so that a pressure drop can be formed between the central outlet opening and the suctional intake opening or openings when additional gas is supplied. It is a further requirement that the suctional intake openings be sufficiently wide in order not to generate an appreciable pressure drop. Also, the suctional intake openings need not be disposed in the wall opposite the outlet opening but can, for example, be provided in the same wall as the outlet opening or in the cylindrical side wall bounding the vortex chamber. Thus, in the embodiment illustrated in FIGS. 14 and 15, a suctional intake opening 2a, communicating with the environment, is provided in the cylindrical wall portion of the vortex chamber (rather than in a radial wall surface as illustrated, for example, in FIGS. 1 and 2). As already indicated above, it is also possible to use two or more tangential inlet nozzles 3 for the additional gas without changing the fundamental way of operation of the construction. In such a case it is feasible to supply different types of additional gases through the various nozzles. In order to illustrate these modifications, FIG. 13 shows an alternative embodiment of a valve construction according to the invention provided, on the one hand, with two tangentially disposed inlet nozzles 3' for additional gas and, on the other hand, with a plurality of suctional intake openings 2'.

It will be understood that the above description of the present invention is susceptible to various modifications, changes and adaptations, and the same are intended to be comprehended within the meaning and range of equivalents of the appended claims.

What I claim is:

1. In a device for administering to a patient a mixture of a first gas and at least one second gas in a desired, predetermined ratio between 0 and 100%, the first gas being supplied to the device by a non-pressurized system and the second gas being supplied to the device under pressure; the device including a self-expanding, lung-venting bladder having an inlet through which the gases are introduced into the bladder and an outlet through which the gases are administered to a patient; a check valve disposed in the zone of the bladder inlet for preventing the gases from escaping from the bladder through the bladder inlet; the bladder being adapted to expand for drawing the gases thereinto through the bladder inlet; the bladder being adapted to be compressed for discharging the gases therefrom through the bladder outlet; the improvement comprising a suction valve having a. a housing means defining a chamber having a first wall and a second wall parallel-spaced from said first wall and a circular wall adjoining said first and second walls;

b. means defining, in said housing means, a valve outlet disposed in said first wall centrally with respect to said chamber, said valve outlet being connected to said bladder inlet for maintaining communication between said chamber and said bladder inlet;

c. means defining, in said housing a suctional intake opening positioned radially outwardly of said valve outlet and being in continuous communication with the non-pressurized system; said bladder, during its expansion, generating a pressure drop from said suctional intake opening to said valve outlet; and d. at least one inlet nozzle extending through said circular wall and supported adjacent said suctional intake opening and being oriented tangentially with respect to said chamber and substantially perpendicular with respect to said valve outlet for injecting said second gas tangentially into said chamber; said inlet nozzle being arranged for controlling, with said second gas, the intake of said first gas by changing said pressure drop in an inverse relationship to the intake of said second gas.

2. The device as defined in claim 1, wherein said chamber is of circular cross section and said suctional intake opening is a slot shaped as an arc of a circle extending along the periphery of said chamber.

3. The device as defined in claim 1, further comprising a gas collecting container having an open end in communication with said suctional intake opening and another end open to the environment.

4. The device as defined in claim 1, wherein said suctional intake opening being positioned in said second wall.

5. The device as defined in claim 1, wherein said circular wall comprises a cylindrical wall and said first and second walls comprise two opposite circular radial walls adjoining said cylindrical wall for defining a cylindrical space constituting said chamber; said suctional intake opening being located in said cylindrical wall.

6. The device as defined in claim 1, wherein said suctional intake opening is constituted by at least one series of individual apertures.

7. The device as defined in claim 6, wherein said chamber is of circular cross section and at least one series of individual apertures extends in an arc of a circle along the periphery of said chamber.

8. The device as defined in claim 1, wherein said circular wall comprises a cylindrical wall and said first and second walls comprise two opposite circular radial walls adjoining said cylindrical wall for defining a cylindrical space constituting said chamber; said valve outlet being positioned in the center of one of said circular radial walls; said suctional intake opening being provided in the other of said circular radial walls; said inlet nozzle being positioned in said cylindrical wall.

9. The device as defined in claim 8, wherein said suctional intake opening is elongated and has an arcuate course parallel to the perimeter of said other circular radial wall; said inlet nozzle having a discharge end situated at one end of, and oriented toward the elongated suctional intake opening.

* * * * *